United States Patent [19]

Arnold

[11] Patent Number: 4,746,489
[45] Date of Patent: May 24, 1988

[54] METHOD FOR DECONTAMINATING AND CLEANING OCULAR PROSTHESES, PARTICULARLY CONTACT LENSES, AND DEVICE FOR IMPLEMENTING SUCH METHOD

[75] Inventor: Noel Arnold, Colmar, France
[73] Assignee: Yves Nold, Thionville, France
[21] Appl. No.: 848,438
[22] PCT Filed: Jul. 3, 1985
[86] PCT No.: PCT/FR85/00184
§ 371 Date: May 5, 1986
§ 102(e) Date: May 5, 1986
[87] PCT Pub. No.: WO86/00721
PCT Pub. Date: Jan. 30, 1986

[30] Foreign Application Priority Data
Jul. 4, 1984 [FR] France ............... 84 10728

[51] Int. Cl.[4] .......... A61L 2/20; A61L 7/00; B01J 19/08
[52] U.S. Cl. ............ 422/29; 422/186.07; 422/292; 422/305; 422/116
[58] Field of Search ............ 422/24, 28, 29, 33, 422/300, 302, 292, 305, 186.07, 116; 206/5.1

[56] References Cited

U.S. PATENT DOCUMENTS

| | | | |
|---|---|---|---|
| 3,473,886 | 10/1969 | Leeds . | |
| 3,549,528 | 12/1970 | Armstrong | 422/28 X |
| 3,852,032 | 12/1974 | Urbach . | |
| 4,063,890 | 12/1977 | Baron | 422/24 |
| 4,179,616 | 12/1979 | Coviello et al. | 422/305 X |

FOREIGN PATENT DOCUMENTS

| | | | |
|---|---|---|---|
| 0079827 | 5/1983 | European Pat. Off. . | |
| 2492665 | 4/1982 | France . | |
| WO83/00447 | 2/1983 | PCT Int'l Appl. . | |
| 1583394 | 1/1981 | United Kingdom | 422/24 |

Primary Examiner—Barry S. Richman
Assistant Examiner—Jill Johnston
Attorney, Agent, or Firm—Young & Thompson

[57] ABSTRACT

Ozone is electrically generated by ionization in an ionizing tube (7). The ozone migrates across a hydrophobic semipermeable membrane (25), and diffuses into an isotonic solution for soaking contact lenses for a predetermined duration, preferably on the order of two hours.

9 Claims, 3 Drawing Sheets

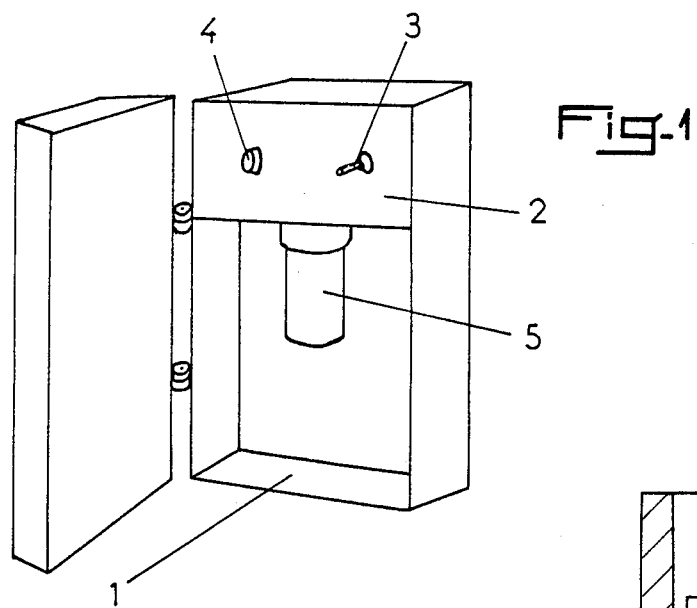
Fig. 1
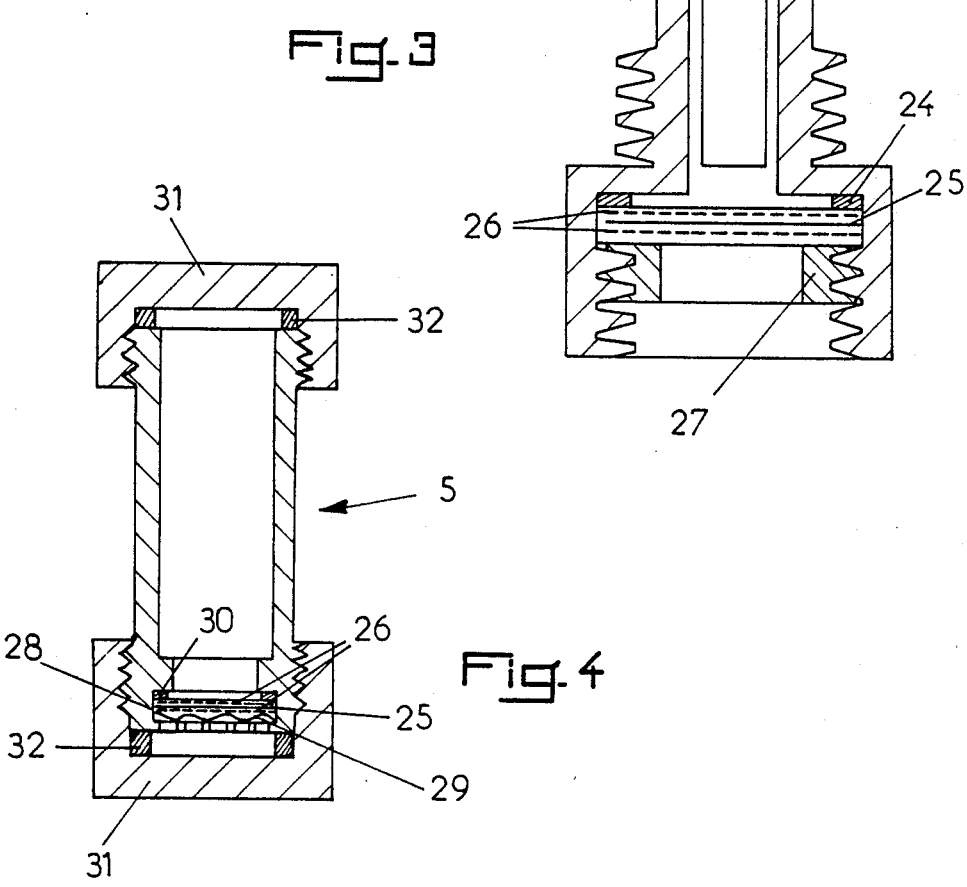
Fig. 3
Fig. 4

METHOD FOR DECONTAMINATING AND CLEANING OCULAR PROSTHESES, PARTICULARLY CONTACT LENSES, AND DEVICE FOR IMPLEMENTING SUCH METHOD

The present invention concerns the field of vision correction devices, and particularly contact lenses, and has as an object a method for decontaminating and cleaning ocular prostheses, particularly contact lenses.

The invention similarly has as an object a device for practicing this method.

BACKGROUND OF THE INVENTION

The human eye equipped with contact lenses, must be protected from microbial infection. One of the problems associated with these lenses resides in their maintenance product. Besides a simplicity of use, this latter requires qualities of microbiological efficiency and cleaning properties.

To this effect, there exist several methods which are classified according to their method of action in two categories, to be known as chemical and physical.

These processes nevertheless have certain inconveniences.

The chemical procedures use isotonic and sterilizing solutions containing preservatives, such as chlorhexidine and gluconate, mercury derivates or quaternary ammonium. The use of these solutions imposes numerous constraining operations on the user. Moreover, reactions of toxicity and ocular irritation are not uncommon.

A second method consists of treating the lenses with a 3% hydrogen peroxide solution. This procedure is efficient from the point of view of germ destruction, but the solution used must be neutralized with a reducing agent or a strong burning in the eye of the user may be provoked.

In the category of physical methods, there can be mentioned boiling, which is a confirmed process for sterilization of water, but which has the disadvantage, in the case of contact lenses, of provoking a lens cloudiness due to the denaturation of the muco-proteic material.

At present, there is thus no method which brings together simplicity of use and absence of undesirable secondary effects.

SUMMARY OF THE INVENTION

The present invention has as an object to overcome these disadvantages.

It has, in effect, as an object a method for decontamination and cleaning of ocular prostheses, particularly contact lenses, characterized in that it consists essentially of producing ozone by ionization in an ionizing tube, causing this ozone to migrate across a filtering membrane and next causing the said ozone to diffuse into an isotonic solution for soaking the lenses for a predetermined duration, preferably on the order of two hours.

The invention similarly has as an object a device for practicing this method, which is characterized in that it is constituted essentially by a box comprising a control panel provided with an on/off switch, a luminous indicator, a removable receptacle for receiving ocular prostheses, and an electric control circuit for an ionizing tube mounted in a cylindrical body fixed in a removable manner to the control panel of the box.

BRIEF DESCRIPTION OF THE DRAWINGS

The invention will be best understood thanks to the following description, which refers to a preferred embodiment, given by way of non-limiting example, and explained with reference to the accompanying schematic drawings, in which:

FIG. 1 is a view in perspective of a device according to the invention;

FIGS. 3 and 4 are views in section of two possible embodiments for the filtration device.

DETAILED DESCRIPTION OF THE INVENTION

Figure 2:
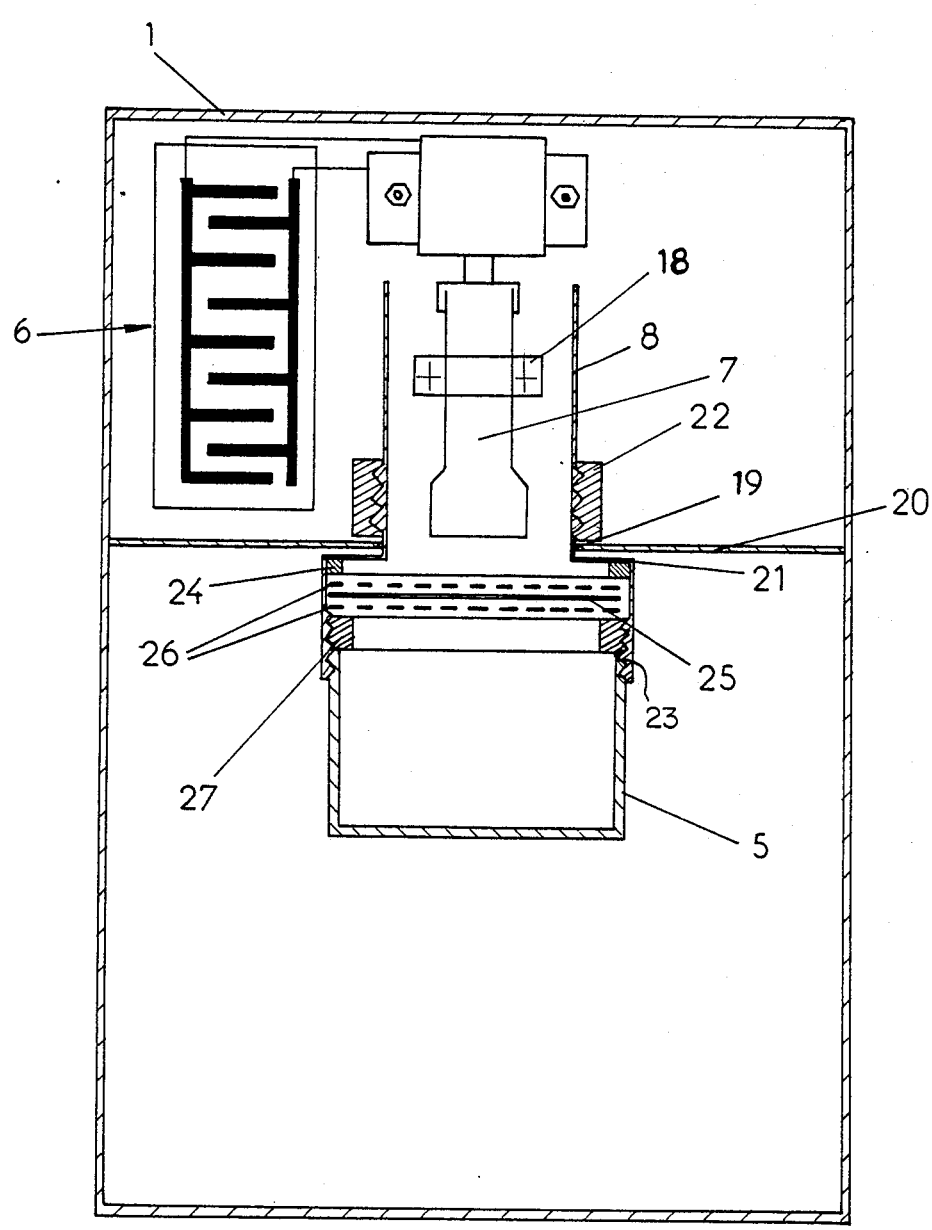
FIG. 2 is a view in section, and on an increased scale of the device according to FIG. 1.
Figure 5:
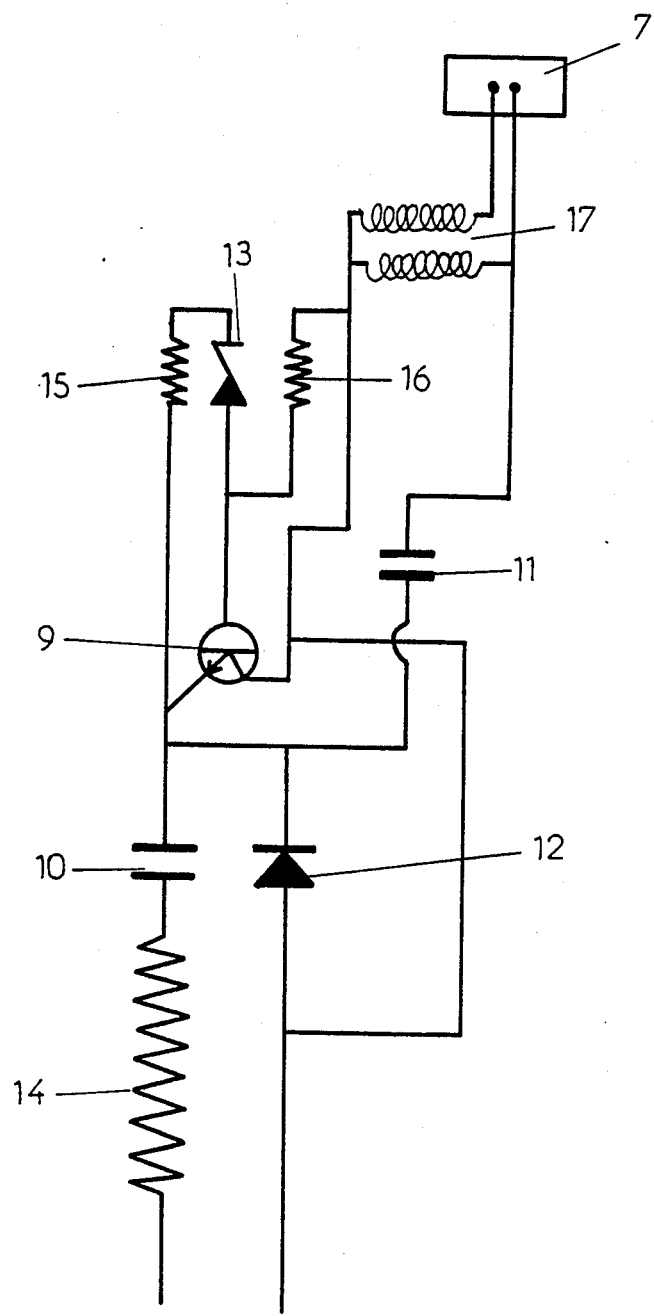
FIG. 5 is a diagram of the electric control circuit.

According to the invention, and as is shown more particularly by way of example, in FIGS. 1 and 2 of the accompanying drawings, the device for practicing the method of decontamination and cleaning of ocular prostheses, and particularly contact lenses, is constituted essentially by a box 1 which comprises a control panel 2 provided with an on/off switch 3, an indicator 4 serving to indicate functioning of the device, a removable receptacle 5 for receiving ocular prostheses fixed under the control panel 2, and an electric control circuit 6 for an ionizing tube 7, which is mounted in a cylindrical body 8, which is fixed in a removable manner to the control panel 2 of the box 1.

On its rear face, it is provided with terminals for connecting the electric circuit 6 to a source of electric current, the electric circuit 6 comprising a transistor 9, two condensers 10 and 11, a diode 12, a Zener diode 13, and three resistors 14 to 16, and supplying the ionizing tube 7 through the intermediary of a transformer 17.

The electric supply may be by direct or alternating current.

The cylindrical body 8 for housing the ionizing tube 7, which is fixed therein by means of holding flaps 18, is preferably formed from a synthetic material and the said cylindrical body 8 is engaged in an opening 19 of the face 20 corresponding to the control panel 2 up to a stop of an enlarged portion 21 of the said body 8, a locking ring 22 assuring the retention of the body 8 in the opening 19.

The cylindrical body 8 has in its enlarged portion 21 an internal threading 23 permitting the tightening, by means of the receptacle 5, of a filtration device constituted by a gasket 24 of chemically inert material, a gas selective filtering membrane 25, and safety grids 26 disposed on both sides of the membrane 25, a tightening ring 27 cooperating with the internal threading 23 assuring the clamping of the device (FIG. 3).

The threading 23 permits a rapid fixation of the receptacle 5 for reception of the ocular prostheses.

The membrane 25 is advantageously an ultra-thin membrane, of the type used in microdialysis, having hydrophobic properties, and is formed, preferably, from silicon or PTFE.

According to one embodiment of the invention, and as is shown in FIG. 4, the filtering device is mounted directly in the receptacle 5 for reception of the ocular prostheses, the filtering membrane 25 and its safety grids 26 being maintained in their housing 28 by means an elastic ring 29, which presses them against the overflow lips 30.

The receptacle 5 is advantageously provided at its two extremities with screw caps 31 whose watertightness is assured by means of toric gaskets 32.

For the treatment of ocular prostheses, one of the caps 31 is removed, and the extremity thus disengaged is fixed on the threading 23 of the cylindrical body 8 of the device by simple screwing.

According to another characteristic of the invention, the switch 3 activates a time delay cutting off the electric supply after a predetermined duration.

The ozone used in the method according to the invention is a chemical agent in the gaseous state, which, under normal conditions of pressure and temperature, is constituted by three oxygen atoms, and which self-destructs, tending to become permanently disassociated according to the transformation: $O_3 \rightarrow O_2 + O$.

The O atoms join two by two to form oxygen $O_2$. Accordingly, the ozone disappears very rapidly when the source which generates it is stopped, and there can be no secondary effect created resulting from its adsorption and its subsequent discharge in the eye of the user.

The device according to the invention has as an object to dissolve the ozone in an isotonic solution for preserving the contact lenses, while mechanically isolating the liquid medium containing the said lenses from the ozone generator, which operates in a dry atmosphere.

The concentration of dissolved ozone in the isotonic solution is comprised between 0.1 mg/l and 10 mg/l. Preferably, the dissolved ozone concentration in the isotonic solution is 1 mg/l.

Moreover, the device according to the invention assures a preservation from any microbiological contamination after the treatment.

The device according to the invention operates in the following manner:

By way of example, reference is made to a lens cleaning and decontamination operation.

First, a receptacle 5 for receiving the lenses is fixed in the connecting opening 23 of the cylindrical body 8 by screwing, until locking is obtained. The terminals of the device are then connected to the mains, and the said device is started by activating the switch 3, and the indicator 4 is illuminated.

The passage of current in the electric circuit 6 supplies the ionizing tube 7, thereby generating ozone, which has a density greater than the ambient air, and which descends into the cylindrical body 8 as far as the filtering device.

The difference of partial pressure between the upper and lower walls of the membrane 25 causes a migration of ozone across the membrane 25 and a diffusion into the soaking liquid for the lenses.

After two hours of functioning, the cleaning and decontaminating operation is terminated, and a stoppage is effected by reversing the switch 3.

Experimentation has shown that a duration of treatment of two hours is sufficient for an efficient cleansing and decontamination.

The tests were made on the following germs:
- *Escherichia coli*
- *Pseudomonas aeruginosa*
- *Staphylococcus aureus*
- *Candida albicans*

The population density in the physiological solution containing the contact lenses, was about $10^6$ germs per ml.

The results obtained may be summarized in the following manner:

The micro-organisms are destroyed in proportions which differ according to the microbial species.

All the germs are killed in the case of *Escherichia coli, Pseudomonas aeruginosa* and *Candida albicans*.

With respect to the *Staphylococcus aureus*, the bacteria are destroyed in a proportion of 99.99%.

It will be noted that the micro-organism concentration chosen is clearly greater than that found in normally contaminated lenses.

Moreover, the efficiency of the cleaning on a series of 20 used lenses having colored deposits, was also tested. This test yielded the following results:

10 lenses became clear and perfectly transparent once again, 8 lenses showed a decreased intensity in the coloration, 2 lenses resisted the treatment.

Finally, supplementary tests have shown that 100 hours of continuous treatment on different types of lenses, did not cause any modification of the infra-red spectrum due to an alteration of the material.

The method and the device according to the invention permit realizing the cleaning and decontamination of contact lenses in an efficient manner and without secondary undesired effects.

The device according to the invention has, moreover, the advantage of a small bulk and a low purchase price.

It will be understood, that the invention is not limited to the embodiment described and shown in the accompanying drawings. Modifications remain possible, particularly from a point of view of the construction of the various elements, or by substitution of equivalent techniques, without departing from the domain of protection of the invention.

I claim:

1. A process for disinfecting ocular prostheses, comprising the steps of generating ozone by ionization in an ionizing tube using an electric circuit, in the absense of ultraviolet radiation; causing said ozone to migrate across a hydrophobic semipermeable membrane; and causing the said ozone to diffuse directly from said membrane into an isotonic solution in which the lenses are immersed for a predetermined duration.

2. Process, according to claim 1, wherein the concentration of ozone dissolved in the isotonic solution is between 0.1 mg/l and 10 mg/l.

3. Process, according to claim 1 wherein the concentration of ozone dissolved in the isotonic solution is 1 mg/l.

4. A device for disinfecting ocular prostheses comprising:

a container having on one of its faces, a control panel provided with an on/off switch and a luminous indicator and being electrically connected to a control circuit means for timing a disinfecting process, a cylindrical body positioned within said container and having an ionizing tube therein, said ionizing tube being electrically connected to said control circuit means for generating ozone in said cylindrical body, means removably connecting a removable receptacle within said container for receiving ocular prostheses to be disinfected, said receptacle being in fluid communication with said cylindrical body and a hydrophobic semipermeable membrane mounted within said container and positioned between said receptacle and said cylindrical body containing said ionizing tube for admitting ozone generated by said ionizing tube into said receptacle for disinfecting prostheses received therein.

5. Device according to claim 4, in which said membrane is selected from the group consisting of silicone and polytetrafluoroethylene.

6. Device, according to claim 4 wherein the cylindrical body is constructed of a synthetic material and is positioned in an opening of the face of the container corresponding to the control panel and locking ring means is positioned in the container so as to secure the cylindrical body in the opening.

7. Device according to claim 4 wherein the on/off switch activates a time delay which opens the control circuit means after a predetermined duration, cutting off the power supply to the device.

8. Device, according to claim 4 wherein the cylindrical body has an enlarged portion with an internal threading permitting the fastening of an externally threaded filtering device within said container between said cylindrical body and said receptacle, said filtering device comprising a watertight gasket contructed of a chemically inert material, the hydrophobic semipermeable membrane and safety grid means being disposed on both sides of said hydrophobic semipermeable membrane, and said enlarged portion of said cylindrical body further comprising a locking ring positioned within said container so as to cooperate with the internal threading to assure clamping of the filtering device within the container.

9. Device, according to claim 8, wherein the filtering device is positioned directly in the receptacle for receiving ocular prostheses, and wherein the hydrophobic semipermeable membrane and the safety grid means are maintained in a housing in said container by means of an elastic ring which presses the hydrophobic semipermeable membrane and the safety grid means against an overflow wall in the filtering device.

* * * * *